United States Patent [19]

Clarkson et al.

[11] Patent Number: 4,853,411

[45] Date of Patent: Aug. 1, 1989

[54] BIOCIDE

[75] Inventors: Douglas Clarkson, Aughton; Richard P. Clifford, South Wirral, both of England

[73] Assignee: W.R. Grace & Co.-Conn., New York, N.Y.

[21] Appl. No.: 131,681

[22] Filed: Dec. 11, 1987

[30] Foreign Application Priority Data

Feb. 3, 1987 [EP] European Pat. Off. ........ 87300948.4

[51] Int. Cl.$^4$ ...................... A01N 43/26; A01N 37/34
[52] U.S. Cl. ..................................... 514/441; 514/520
[58] Field of Search ............................... 514/441, 520

[56] References Cited

U.S. PATENT DOCUMENTS

| | | | |
|---|---|---|---|
| 3,790,677 | 2/1974 | Bader et al. | 142/12 |
| 3,873,711 | 3/1975 | Brink, Jr. et al. | 514/441 |
| 3,873,712 | 3/1975 | Brink, Jr. et al. | 514/441 |
| 3,876,792 | 4/1975 | Brink, Jr. et al. | 514/441 |
| 3,879,513 | 4/1975 | Shema et al. | 514/441 |
| 3,903,290 | 9/1975 | Shema et al. | 514/441 |
| 3,996,378 | 12/1976 | Payton | 142/42 |
| 4,069,341 | 1/1978 | Pierce | 604/304 |
| 4,079,148 | 3/1978 | Oeckl et al. | 514/520 |
| 4,188,376 | 2/1980 | Payne et al. | 514/373 |
| 4,289,581 | 9/1981 | Katayama et al. | 514/441 |
| 4,344,957 | 6/1982 | Katayama et al. | 162/161 |
| 4,379,137 | 4/1983 | Ehlers et al. | 424/78 |
| 4,464,146 | 6/1984 | Borovian | 474/133 |
| 4,466,975 | 8/1984 | Magami et al. | 514/373 |
| 4,518,610 | 5/1985 | Umekawa et al. | 514/516 |
| 4,616,037 | 10/1986 | LeMarre et al. | 514/515 |
| 4,647,577 | 3/1987 | Umekawa et al. | 514/441 |

FOREIGN PATENT DOCUMENTS

| | | |
|---|---|---|
| 0209260 | 1/1987 | European Pat. Off. . |
| 3201761 | 9/1983 | Fed. Rep. of Germany . |
| 2296623 | 7/1976 | France . |
| 1519329 | 7/1978 | United Kingdom . |
| 2022416 | 12/1979 | United Kingdom . |
| 2092446 | 8/1982 | United Kingdom . |
| 2098067 | 11/1982 | United Kingdom . |
| 2138799 | 10/1984 | United Kingdom . |

OTHER PUBLICATIONS

5/77 Japanese Patent Reports, Chemical, vol. 77, No. 16, p. 3.
1973 Chemical Abstracts vol. 79, p. 160, 74928m.
1976 Chemical Abstracts vol. 84, pp. 171, 379, 505, 84:59271b, 84:55305t.
1977 Chemical Abstracts vol. 86, pp. 150, 297, 86:166406n.
1980 Chemical Abstracts vol. 92, pp. 358, 428 92:116475n.
1980 Chemical Abstracts vol. 93, p. 732, 93:114497t.
1981 Chemical Abstracts vol. 94, p. 202, 94:115999v.
1981 Chemical Abstracts vol. 95, pp. 223, 226 95:199029f.
1982 Chemical Abstracts vol. 96, pp. 194, 238 117585t.
1982 Chemical Abstracts vol. 97, pp. 187, 257, 331, 97:140275w, 115139x, 97:34703z.
1983 Chemical Abstracts vol. 98, p. 195, 98:138972y, 98:138970w.
1984 Chemical Abstracts vol. 101, p. 611 101:7142k.
1985 Chemical Abstracts vol. 102, pp. 222–223, 338, 102:199590v, 102:154614q.
1985 Chemical Abstracts vol. 103, p. 514, 103:37469f.
1986 Chemical Abstracts vol. 104, pp. 243, 265, 104:1439966w, 104:104459p.
Res. Disclosure 22520.

*Primary Examiner*—Allen J. Robinson
*Assistant Examiner*—Raymond J. Henley, III
*Attorney, Agent, or Firm*—David E. Heiser

[57] ABSTRACT

A method of treating an aqueous or non-aqueous dfsystem is disclosed which comprises adding to the system a thiolan of the formula

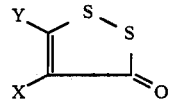

wherein each of X and Y, which may be the same or different, represents fluorine, chlorine or bromine, in combination with a sulphone of the formula:

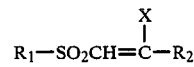

in which $R_1$ represents an optionally halogenated alkyl radical or an optionally substituted aryl radical, $R_2$ represents a cyano or amidocarbonyl radical and X represents a halogen atom.

16 Claims, No Drawings

BIOCIDE

This invention relates to the treatment of aqueous systems, especially cooling water systems and water systems used in paper pulping and manufacture, as well as non-aqueous systems which can be termed functional fluids.

In industrial cooling water systems, for instance in industrial cooling towers, the water used is not, of course, sterile with the result that bacteria accumulate in the system and this quite commonly gives rise to a slimy deposit on the surfaces of the system which come into direct contact with the cooling water. A similar situation applies in paper making; slime can deposit on any of the surfaces with which the water comes into contact including the paper pulping bath, on the paper web and in the recirculating back pipework. Again such problems arise in the extraction and refining of sugar.

A large variety of different microbiological control agents have been used for the purpose of killing these bacteria and/or inhibiting slime formation or for dispersing and killing microbiological slime. These chemicals are principally biostats such as lime or sulphur dioxide or, more generally, biocides, for example isothiazolones, methylene bis(thiocyanate), quaternary ammonium compounds and chlorine release agents.

One such biocide is 5-oxo-3,4-dichloro-1,2-dithiolan (or 4,5-dichloro-1,2-dithiol-3-one) which has the formula:

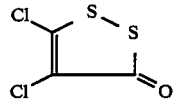

A particular requirement for an effective industrial biocide for aqueous systems is a capability to rapidly reduce the level of bacterial infections within such systems whilst also imparting long term protection to the system from future microbiological ingresses. Diothiolan is known to be rapid-acting, principally against gram negative bacteria. However because it is rapidly-acting it does not last long in the system such that the latter has to be dosed at fairly frequent intrevals. It has now been found, according to the present invention, that such a biocide when used in combination with a specific different type of biocide, not only is effective over a prolonged period but also behaves synergically.

According to the present invention there is provided a method of treating an aqueous or non-aqueous system which comprises adding to the system a thiolan of the formula:

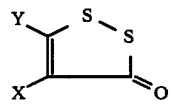

wherein each of X and Y, which may be the same or different, represents fluorine, chlorine or bromine, in combination with a sulphone of the formula:

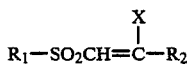

in which $R_1$ represents an optionally halogenated alkyl radical, generally with 1 to 8, especially 1 to 4, carbon atoms, or an optionally substituted aryl radical, $R_2$ represents a cyano or amidocarbonyl radical and X represents a halogen atom. The halogen atoms are preferably chlorine atoms.

Examples of the radicals $R_1$ include straight-chain and branched-chain alkyl radicals, in particular methyl and ethyl radicals as well as phenyl and naphthyl radicals, optionally substituted by one or more halogen, alkyl, alkoxy, halogenoalkyl, nitro or hydroxyl radicals.

Preferred compounds for use in the present invention include those in which $R_1$ represents methyl, phenyl, 3-chlorophenyl, 3,4-dichlorophenyl, 3-nitrophenyl, 4-methylphenyl or 4-chloromethylphenyl.

Particularly preferred is phenyl-(2-cyano-2-chlorovinyl)-sulphone i.e. $R_1$ represents phenyl, $R_2$ represents cyano and X represents chlorine. This compound is available commercially from Bayer as the Sulphone Preventol® VPOC3036 in association with phenyl-(1,2-dichloro-2-cyanovinyl)sulphone and phenylsulphonyl propionitrile.

The first component is preferably one in which X and Y represent chlorine i.e. 4,5-dichloro-1,2-dithiol-3-one. This compound is known from, for example, Japanese Patent Publication No. 14294/1977. It can be prepared by, for example, heating 1,1,2,3,3,3-hexachloroprop-1-ene, or the intermediate 2,3,3-trichloro-propenoic acid, with sulphur and steam (see, for example, DE-A No. 32-1761). The other compounds can be prepared similarly from the corresponding 2,3,3-trihalo-propenoic acids.

Although it will normally be more convenient to add the thiolan and sulphone as a mxture it is, of course, possible to add them separately. In such circumstances the thiolan is suitably added as a solution in a solvent; the sulphone will, in general, be a liquid which can be added direct; for ease of control they are added as a dilute solution in an appropriate solvent. The present invention also provides a composition suitable for addition to an aqueous system which comprises at least one thiolan as defined above and at least one sulphone as defined above.

The present invention finds utility in a variety of different aqueous systems including those used in the extraction and refining of sugars, as well as in functional fluids or oils, for example cutting oils and heavy oil sludges, in paint systems and in the textile industry in finishing agents and conditioners but, more particularly in the paper-making industry and in cooling water systems. The compositions are effective against both fungal and bacterial contaminants of such systems.

In paper making, the active ingredients may be added to the paper pulping bath, the recirculating backwater, or, for example, to a holding tank containing generally moist, pulp or along with one or more chemical additives used in paper making or containing starch or paper coating masses. Such additives include starch, for example potato or corn starch, titanium dioxide, a defoamer such as a fatty acid alcohol, a size for example a rosin size based on abietic acid, a neutral size based on alkyl ketene dimer or a succinic acid anhydride based size, a wet strength resin such as, if neutral, an epichlorohydrin polyamide or, if acid, a melamine- or urea-formaldehyde resin, various polymers used as dispersants or retention aids such as polyacrylates, polymethacrylates, polyamides and polyacrylamides, clay, chalk, fillers such as carboxymethyl cellulose, polyvinyl alcohol and optical brightening agents.

In cooling water systems, the active ingredients may be introduced at any location where they will be quickly and efficiently mixed with the water of the system although it will generally be most convenient to add them to the make-up or feed water lines through which the water enters the system. Typically, an injector calibrated to deliver a pre-determined amount periodically or continuously to the make-up water is employed. Of course, conventional water treatment additives such as corrosion inhibitors and lignin derivatives can also be included.

If the thiolan and sulphone are added as a composition, the total concentration of the active ingredients will, in general, be from 0.1 to 20% by weight, preferably from 2 to 8% by weight. The amount of sulphone (by weight) will generally exceed that of the thiolan. In general the weight ratio of the thiolan to the sulphone is from 1:40 to 1:1, preferably from 1:15 to 1:1.2, more preferably from 1:5 to 1:1.2. Clearly, if the ingredients are added separately the same relative concentrations apply.

The amount of the combination (active ingredient) added to the system will normally be from 0.1 to 40 ppm, preferably from 0.4 to 40 ppm. The concentration of biocides will, of course, vary depending on the nature of the biocides and on the nature and amount of the bacteria present but, clearly, an amount effective to control the bacteria present should be used.

The active ingredients are suitably formulated as a liquid composition but they may also be used in the form of, say, a powder.

The solvents used in the liquid preparation are preferably organic solvents and especially substantially anhydrous organic solvents because 4,5-dichloro-1,2-dithiol-3-one tends to hydrolyse in the presence of water. Preferably hydrophilic solvents which can dissolve the active ingredients, are miscible with water and can give storable, stable compositions are used unless, of course, the composition is to be added to, say, a cutting fluid in which an oil-soluble solvent such as a hydrocarbon solvent is generally used. Examples of suitable hydrophilic solvents include glycols, such as ethylene glycol, propylene glycol, diethylene glycol and dipropylene glycol; glycol ethers, such as 2-methyoxyethanol, 2-ethoxyethanol, 2-phenoxyethanol, diethylene glycol monomethyl ether, propylene glycol monomethyl ether, dipropylene glycol monomethyl ether and tripropylene glycol monomethyl ether; and alcohols containing up to 8 carbon atoms. Mixtures of two or more solvents may also be used. Butyl diglycol and polyethylene glycols are particularly preferred, for example, those having a molecular weight of 190 to 210; also preferred are 2-butoxyethanol, propylene glycol, polypropylene glycols and diethylene glycol.

The composition may also contain one or more dispersing agents. Examples of suitable dispersing agents include cationic, anionic, non-ionic or amphoteric surfactants; non-ionic surfactants are preferred. Typical surfactants which can be used include ethylene oxide adducts, especially ethoxylated phenols having the general formula:

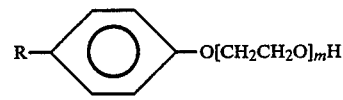

where m represents 2 to 40 and R represents $C_n H_{2n+1}$ in which n is from 0 to 18, as well as alkylamine-polyoxypropylene-polyoxyethylene adducts and alkylolamides.

Preferred ethoxylates are those derived from phenol itself, nonyl phenol and dodecyl phenol and those containing 4 to 15 ethoxylate groupings. Especially preferred is "Ethylan HB4 Clankro, UK)" which is a phenol ethoxylate containing about 4 ethoxylate units. Typical alkylamine polyoxypropylene polyoxyethylene adducts include N,N,N',N'-Polyoxyethylene-polyoxypropylene-ethylenediamine block copolymers, for example those having the formula:

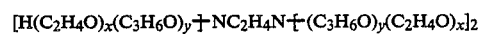

in which each x and each y has a value which can differ from one block to the next. These materials are available commercially as "TETRONICS", varying in molecular weight and the relatives proportions of ethylene oxide and propylene oxide units; in general the ethylene oxide units represent 10 to 80% by weight of the product while propylene units provide a molecular weight of, say, 2,000 to 25,000.

Typical alkylolamides which can be used include those obtained from a fatty acid containing, say, 8 to 18 carbon atoms, for example coconut fatty acids, and an alkanolamine, preferably ethanolamine or diethanolamine. Some such materials are available commercially under the trade marks Concensate (Continental Chemical Company, U.S.A.).

Typically the dispersant to biocide will be from 1:20 to 200:1 ratio of preferably from 1:1.6 to 1.25:1.

The following Examples further illustrate the present invention. In these Examples active ingredient (I) is 5-oxo-3,4-dichloro-1,2-dithiolan while active ingredient (II) is the Sulphone Preventol® UPOC3036 (Bayer, Germany).

EXAMPLE 1

A product with the following formulation:

| Active Ingredient (I) | 1.5% | |
| Active Ingredient (II) | 6.25% | (40% active ingredient) |
| Polyethylene Glycol (M.W. = 190–210) | 92.25% | | was added to a cell suspension of the bacterial species *Pseudomonas fluorescens* at concentrations of 10, 25 and 50 ppm. The pH of the suspension medium was 7.1 and its temperature was 22.5° C. The ratio of active ingredients (I) and (II) was 1:1.6.

The results tabulated below are expressed in terms of percentage survival of bacterial cells following exposure to the biocide for 0.5, 2.0 and 4.0 hours. Formulations included in the experiment in order to determine synergistic interactions are shown below.

| Control A | | Control B | |
|---|---|---|---|
| Active Ingredient (I) | 2.0% | Active Ingredient (II) (40% active ingredient) | 25.0% |
| Polyethylene Glycol (M.W. = 190–210) | 98.0% | Polyethylene Glycol (M.W. = 190–210) | 75.0% |

| Biocide Contact period (Hrs) | Biocide | Biocide Concentration (ppm) | | |
|---|---|---|---|---|
| | | 10 | 25 | 50 |
| 0.5 | Experimental Blend | 6 | 1.5 | 0.13 |
| | Control A | 18.5 | 5.5 | 0.6 |
| | Control B | 90.0 | 80.0 | 41.0 |
| 2.0 | Experimental Blend | 3.2 | 0.25 | 0.02 |
| | Control A | 11.15 | 1.75 | 0.04 |
| | Control B | 65.0 | 60.0 | 38.0 |
| 4.0 | Experimental Blend | 2.55 | 0.17 | 0.01 |
| | Control A | 10.0 | 1.2 | 0.06 |
| | Control B | 46.5 | 30.5 | 14.5 |

These results demonstrate the synergistic interaction of the components of the experimental blend with respect to a bacterial species.

EXAMPLE 2

The formulations used in Example 1 were added to a spore suspension of the fungal species *Aspergillus niger* at concentrations of 50, 100 and 200 ppm. The pH of the suspension was 6.9 and its temperature was 30° C. The ratio of active ingredients (I) and (II) was 1:1.6.

The results tabulated below are expressed in terms of percentage survival of fungal spores following exposure to the biocide for 0.5, 1.0, 2.0 and 4.0 hours. Formulations included in the experiment in order to determine synergistic interaction have been previously described in Example 1.

| Biocide Contact Period (Hrs) | Biocide | Biocide Concentration (ppm) | | |
|---|---|---|---|---|
| | | 50 | 100 | 200 |
| 0.5 | Experimental Blend | 21.4 | 1.2 | NIL |
| | Control A | 34.5 | 1.2 | NIL |
| | Control B | 88.0 | 39.3 | 17.9 |
| 1.0 | Experimental Blend | 19.5 | NIL | NIL |
| | Control A | 27.3 | 1.2 | NIL |
| | Control B | 84.4 | 33.8 | 10.4 |
| 2.0 | Experimental Blend | 13.7 | NIL | NIL |
| | Control A | 24.7 | NIL | NIL |
| | Control B | 83.6 | 23.3 | 5.5 |
| 4.0 | Experimental Blend | 12.2 | NIL | NIL |
| | Control A | 18.4 | NIL | NIL |
| | Control B | 60.2 | 10.2 | 1.0 |

These results demonstrate the synergistic interaction of the components of the experimental blend with respect to a fungal species.

EXAMPLE 3

A product with the following formulation

| Active Ingredient (I) | 0.5% | |
| Active Ingredient (II) | 18.75% | (40% active ingredient) |
| Polyethylene Glycol | 80.75% | | was added to a spore suspension of the fungal species *Aspergillus niger* at concentration of 50, 100 and 200 ppm. The pH of the suspension was 6.9 and its temperature was 22° C. The ratio of active ingredients (I) and (II) was 1:15.

The results tabulated below are expressed in terms of percentage survival of fungal spores following exposure to the biocide for 0.5, 1.0, 2.0 and 4.0 hours.

| Biocide Contact Period (Hrs) | Biocide | Biocide Concentration (ppm) | | |
|---|---|---|---|---|
| | | 50 | 100 | 200 |
| 0.5 | Experimental Blend | 30.95 | NIL | NIL |
| | Control A | 34.50 | 1.2 | NIL |
| | Control B | 88.0 | 39.3 | 17.9 |
| 1.0 | Experimental Blend | 18.2 | NIL | NIL |
| | Control A | 27.3 | 1.2 | NIL |
| | Control B | 84.4 | 33.8 | 10.4 |
| 2.0 | Experimental Blend | 6.8 | NIL | NIL |
| | Control A | 24.7 | NIL | NIL |
| | Control B | 83.6 | 23.3 | 5.5 |
| 4.0 | Experimental Blend | 3.1 | NIL | NIL |
| | Control A | 18.4 | NIL | NIL |
| | Control B | 60.2 | 10.2 | 1.0 |

These results also demonstrate the synergistic interaction of the components of the experimental blend with respect to a fungal species.

We claim:

1. A biocidal composition suitable for addition to an aqueous system which comprises a synergistically effective combination of a thiolan of the formula:

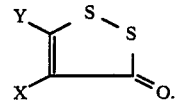

wherein each of X and Y represents chlorine, and a sulphone of the formula:

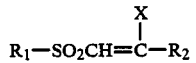

in which $R_1$ represents a phenyl radical, $R_2$ represents a cyano radical and X represents chlorine; the thiolan and the sulphone being present in a weight ratio of the thiolan to the sulphone of from about 1:15 to 1:1.

2. A composition according to claim 1, in which the weight ratio of the thiolan to the sulphone is from about 1:5 to 1:1.2.

3. A composition according to claim 1 in which the weight ratio of thiolan to sulphone is from 1:15 to 1:1.2.

4. A composition according to claim 1 which comprises in addition to said active ingredients, a solvent and optionally a dispersing agent, and which contains a total of from 2% to 8% by weight of the active ingredients.

5. A composition according to claim 1 which is in the form of a solution in a hydrophilic organic solvent.

6. A composition according to claim 5 in which the solvent is butyl diglycol, a polyethylene glycol, 2-butoxy ethanol, propylene glycol, a polypropylene glycol or diethylene glycol.

7. A composition according to claim 1 which also contains a dispersing agent.

8. A composition according to claim 7 in which the dispersing agent is an ethoxylated phenol having the general formula:

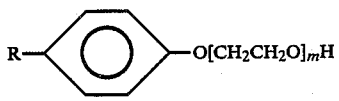

where m represents 2 to 40 and R represents $C_nH_{2n+1}$ in which n is from 0 to 18.

9. A composition according to claim 7 in which the ratio of dispersing agent to active ingredient is from 1:1.6 to 1.25:1.

10. A method of treating an aqueous or non-aqueous system containing fungal or bacterial contaminants or both, to control said contaminants, which comprises adding to the system a thiolan of the formula

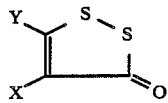

wherein each of X and Y represents chlorine, in combination with a sulphone of the formula:

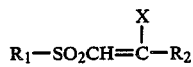

in which $R_1$ represents a phenyl radical, $R_2$ represents a cyano radical and X represents chlorine; the thiolan and the sulphone being added to the system in a weight ratio of the thiolan to the sulphone of from about 1:15 to 1:1 and in amounts effective for said thiolan and said sulphone to provide interactive protection of the system from said contaminants.

11. A method according to claim 10 in which the weight ratio of the thiolan to the sulphone is from about 1:5 to 1:1.2.

12. A method according to claim 10 in which the system is a water-cooling or an aqueous system used in paper-making.

13. A method according to claim 10 in which the weight ratio of thiolan to sulphone is from 1:15 to 1:1.2.

14. A method according to claim 10 in which the combination of active ingredients is added in an amount from 0.1 to 40 ppm.

15. A method according to claim 10 for treating a cooling water system or an aqueous system used in paper-making which comprises adding to the system said thiolan and said sulphone in a weight ratio of 1:15 to 1:1.2, the total concentration of thiolan and sulphone being from 0.1 to 40 ppm.

16. A method according to claim 10 wherein both fungal and bacterial contaminants are present in the system prior to treatment.

* * * * *